US00PP34463P3

(12) United States Plant Patent
Olesen

(10) Patent No.: US PP34,463 P3
(45) Date of Patent: Aug. 2, 2022

(54) **COMPACT *FLORIBUNDA* ROSE PLANT NAMED 'POULPAL091'**

(50) Latin Name: *Rosa hybrida*
Varietal Denomination: Poulpal091

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/300,614

(22) Filed: Sep. 7, 2021

(65) Prior Publication Data

US 2022/0095512 P1 Mar. 24, 2022

(51) Int. Cl.
*A01H 5/02* (2018.01)
*A01H 6/74* (2018.01)

(52) U.S. Cl.
USPC ..... Plt./151
CPC ..... *A01H 6/749* (2018.05)

(58) Field of Classification Search
USPC ..... Plt./101, 141, 151
See application file for complete search history.

(56) References Cited

PUBLICATIONS

Poulsen Roser A/S website citation for 'Coburg' (Poulpal091). 2021. https://www.poulsenroser.dk/fr/roses/ShowProduct/60374. 2 pgs. (Year: 2021).*

* cited by examiner

*Primary Examiner* — Karen M Redden

(57) ABSTRACT

A new garden rose plant of the Compact *Floribunda* class which has abundant, red purple flowers and attractive foliage. This new and distinct variety has shown to be uniform and stable in the resulting generations from asexual propagation.

2 Drawing Sheets

Botanical designation: *Rosa hybrida.*
Variety denomination: 'Poulpal091'.

This application claims priority to Plant Breeder's Rights Application Number 2020/2259, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpal091', originated as a single seedling from the stated cross.

The new variety may be distinguished from its male pollen parent and female seed parent primarily by the following characteristics. The male pollen parent plant has Orange Red 33C flowers while the new variety has Open flowers are Red-Purple Group N57A flowers. The female seed parent plant has red flowers while the new variety has Open flowers are Red-Purple Group N57A flowers.

The objective of the hybridization of this rose variety was to create a new and distinct variety with unique qualities, such as:

1. Uniform and abundant red purple flowers;

2. Vigorous, but compact growth when propagated on its own roots;
3. Exceptional disease resistance.

This combination of qualities is not present in previously available commercial cultivars of this type, known to the inventor, and distinguish 'Poulpal091' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpal091' was selected in the spring of 2012 by the inventor as a single plant from the progeny of the aforementioned hybridization.

Asexual reproduction of 'Poulpal091' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpal091' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal091'.

Specifically illustrated in FIG. 1 of the drawings are flower buds, open flowers viewed from above and from the side, petals and sepals detached showing reproductive flower parts and receptacle.

Figure 1:
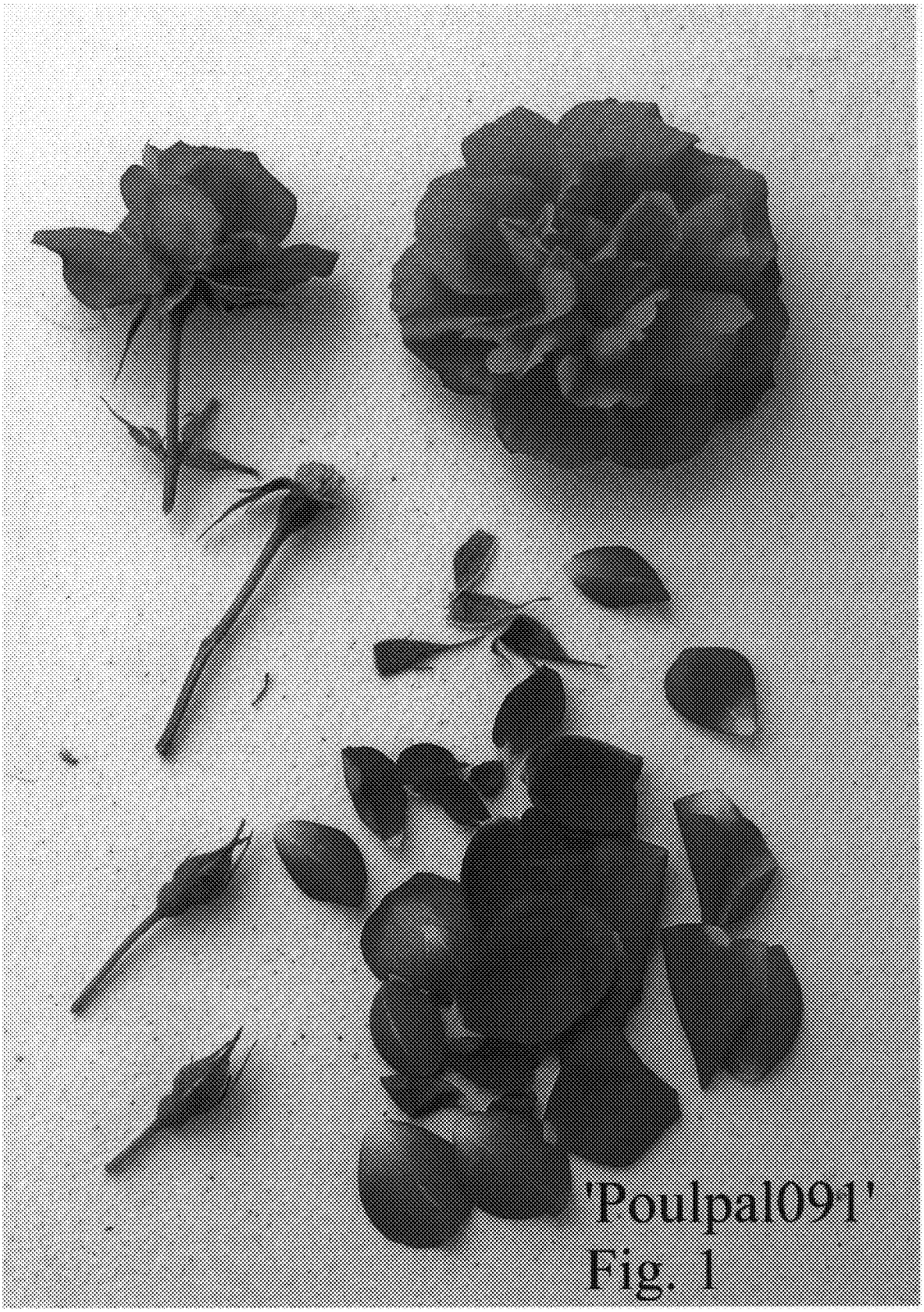
Figure 2:
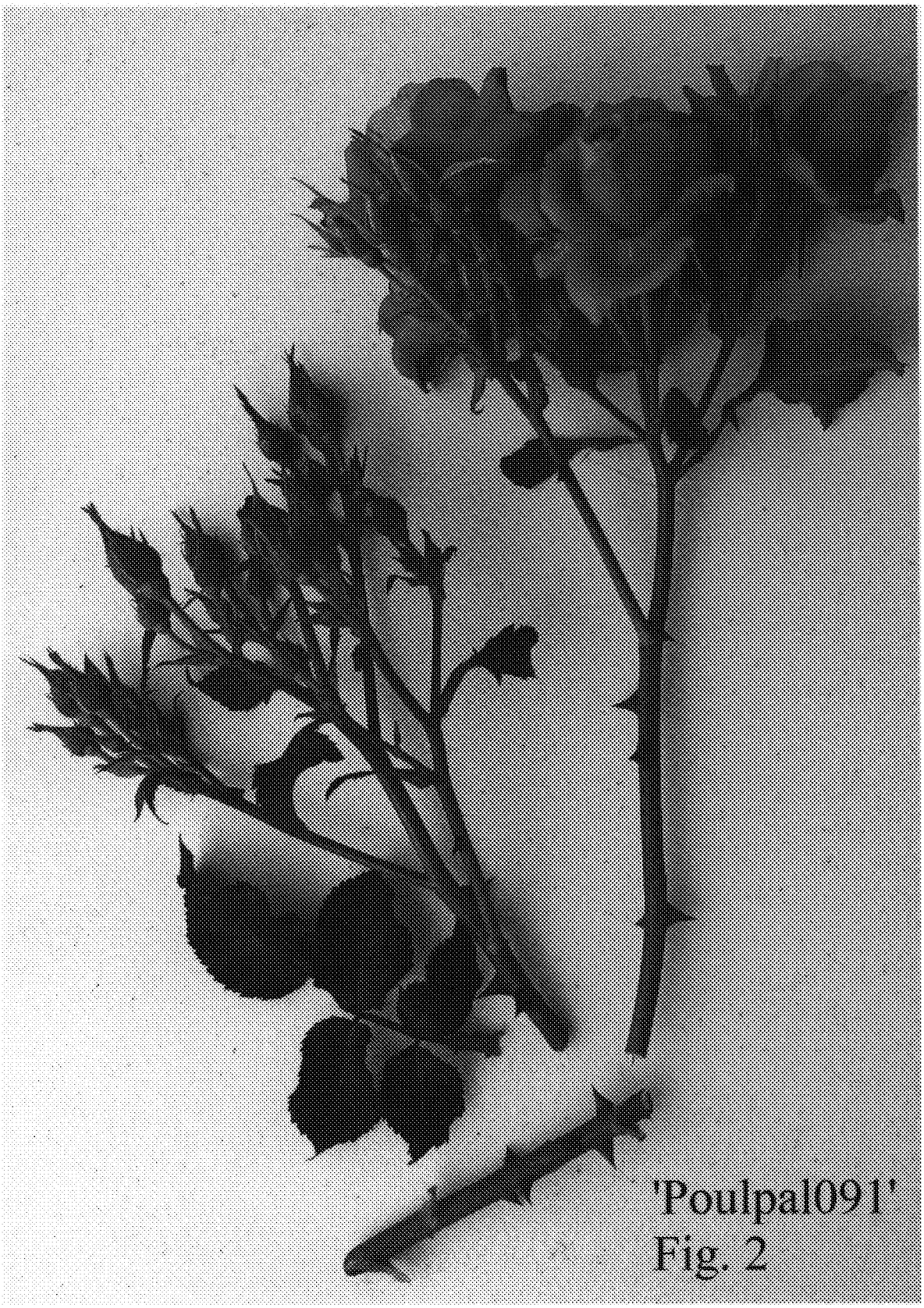

Specifically illustrated in FIG. 2 of the drawings are a cluster of open flowers on the branch, a cluster of flower buds on the branch, bare stem and a mature compound leaf. Plants shown are 2 years of age.

DETAILED DESCRIPTION OF THE VARIETY

The following is a description of 'Poulpal091', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcas031', U.S. Plant Pat. No. 22,502 are compared to 'Poulpal091' in Chart 1.

CHART 1

| | 'Poulpal091' | 'Poulcas031' |
|---|---|---|
| Petal Count | 30 | 40 to 50 |
| Flower Diameter | 80 mm | 70 to 80 mm |
| General Tonality of Flower Color | Open flowers are Red-Purple Group N57A with intonations of Red Group 468 | Red-Purple Group N57A |
| Scent | Moderate to strong honey like perfume | Medium floral scent |

Flower and flower bud:

*Blooming habit.*—Continuous.

*Flower bud.*—Size: Upon opening, 30 mm in length from base of receptacle to end of bud. Bud diameter is about 13 mm. Bud form: Ovoid. Bud color: As sepals divide petals are Red-Purple Group 59C. Sepal inner surface: Color: Yellow-Green Group 144B with intonations of Greyed-Orange Group 174A. Surface: Lightly pubescent. Sepal outer surface: Color: Yellow-Green Group 144A with intonations of Greyed-Red Group 178A. Texture: Smooth. Sepal Shape: Apex: Cirrhose. Base: Flat at union with receptacle. Sepal Margin: Margins have weak foliaceous appendages on three of the five sepals. Sepal size: 26 mm long, 8 mm wide. Receptacle: Texture: Smooth. Size: 11 mm in height, 10 mm wide. Color: Yellow-Green Group 144A. Shape: Campanulate. Pedicel: Surface: Smooth. Length: About 30 mm. Diameter: 2.5 mm. Color: Yellow-Green Group 144A with intonations of Greyed-Purple 184A. Strength: Strong. Peduncle: Length: 3 to 6 cm. Diameter: About 3 mm. Color: Yellow-Green Group 144A with shades of Greyed-Red Group 178B. Texture: Smooth.

*Flower bud development.*—Flower buds are borne in clusters of 9 to 12 flower buds per stem. Development as a panicle.

*Flower bloom.*—Fragrance: Honey like moderate to strong perfume. Duration: The blooms have a duration on the plant of approximately 15 days. Petals fall cleanly away from plant after flowers have fully matured. Size: Flower diameter is 80 mm when open. Flower depth is 40 mm. Flower shape: Fully open flowers are peony or pompon shaped. Shape of flower, side view: The upper portion is concave. The lower portion is convex.

*Petalage.*—Under normal conditions, flowers have about 30 petals.

*General tonality of flower.*—Open flowers are Red-Purple Group N57A with intonations of Red Group 46B.

*Petal color.*—Upon opening, outer petals. Upper surface: Red Group 46B. Lower surface: Red-Purple Group N57B splashed with Red-Purple Group 62B. Upon opening, inner petals: Upper surface: Red Group 46B. Lower surface: Red-Purple Group N57B splashed with Red-Purple Group 62B. Basal petal spots, upon opening: Upper surface: Yellow Group 7A. Lower surface: Yellow Group 7A. After opening, outer petals. Upper surface: Red-Purple Group N57A. Lower surface: Red-Purple Group N57B splashed with Red-Purple Group 62C. After opening, inner petals: Upper surface: Red-Purple Group N57A. Lower surface: Red-Purple Group N57B splashed with Red-Purple Group 62C. Basal petal spots, after opening: Upper surface: Yellow Group 10D. Lower surface: Yellow Group 10D.

*Petals.*—Petal Reflex: Somewhat reflexed. Margin: Entire and uniform. Moderate to strong undulations. Shape: Elliptic. Apex shape: Rounded. Base shape: Acute. Size: 40 mm (l)×29 mm (w). Texture: Smooth. Thickness: Average.

*Petaloids.*—Size: 13 mm (l) by 10 mm (w). Quantity: About 9. Shape: Elliptical with an acute base and rounded apices. Color: On the upper side Red Group 46B. Lower Red-Purple Group N57B splashed with Red-Purple Group 62B. Petaloid spots are Yellow Group 7A on both sides.

*Reproductive flower parts.*—Pollen: None observed. Anthers: Size: 2 mm in length. Color: Yellow-Orange Group 21A. Quantity: 30 on average. Filaments: Color: Yellow-Orange Group 22B. Length: 4 mm. Pistils: Length: 5 mm. Quantity: 28 on average. Stigmas: Color: Greyed-Yellow Group 160D. Styles: Color: Greyed-Yellow Group 160D. Location of stigmas: Inferior in location relative to the length of the filaments and the height of the anthers. Hips: None Observed.

Plant:

*Plant growth.*—Upright, very compact, and bushy. Plants are about 38 cm in height, and 35 cm wide.

*Stems.*—Color of juvenile growth: Yellow-Green Group 144B. Color of mature growth: Yellow-Green Group 144A. Length: Canes are about 16 cm from the base of the plant to the flowering portion. Diameter: About 5 mm. Internodes: On mature canes about 30 mm between nodes. Surface Texture: Young wood: Smooth. Older wood: Smooth.

*Long prickles.*—Incidence: 8 to 10 prickles per 10 cm of stem. Size: Average length of prickles on mature stems is 10 mm. Shape: Upper portion is concave. Lower portion is concave. Color: Juvenile prickles: Greyed-Purple Group 184B. Mature prickles: Greyed-Purple Group 184B.

*Plant foliage.*—Compound leaf: About 114 mm (l)×90 (w). Quantity: 3 leaves per 10 cm of stem on average. Leaf bearing angle to the stem: 45 degrees. Color of juvenile foliage: Upper side: Yellow-Green Group 144A. Lower side: Yellow-Green Group 144B. Color of mature foliage: Upper side: Yellow-Green Group 147A. Lower side: Yellow-Green Group 147C with intonations of Greyed-Purple Group 183A.

*Plant leaves and leaflets.*—Stipules: Size: 15 mm long, 4 mm wide. Quantity: 2 per compound leaf. Shape: Linear, slightly broad based with outward extending apices. Margins: Finely serrated. Color: Yellow-Green Group 144A with intonations of Greyed-Purple Group 184B. Petiole: Length: 20 mm. Diameter: 2 mm. Upper surface color: Yellow-Green Group 144A with intonations of Greyed-Purple Group 184B. Lower surface color: Yellow-Green Group 144A. Rachis: Length: 33 mm. Upper surface color: Yellow-Green Group 144A with intonations of Greyed-Purple Group 184B. Lower surface color: Yellow-Green Group 144A. Leaflet: Quantity: Normally 5 leaflets. Margins: Double serrated. Size: Terminal leaflets are about 56 mm long, 37 mm wide. Shape: Generally elliptical. Base: Rounded. Apex: Mucronate. Texture: Smooth. Thickness: Average. Arrangement: Odd pinnate. Venation: Reticulate. Glossiness: Very glossy.

*Disease resistance.*—Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

*Cold hardiness.*—The variety is tolerant to USDA Cold Hardiness Zone 6.

*Heat tolerance.*—The variety has been found to be suitable for climate conditions found in The American Horticulture Society heat zone 7.

I claim:

1. A new and distinct variety of rose plant of the Compact *Floribunda* rose class named 'Poulpal091', substantially as illustrated and described herein, due to its abundant red purple flowers, disease resistance, and extended period of bloom.

* * * * *

'Poulpal091'

'Poulpal091'